(12) United States Patent
Lee

(10) Patent No.: US 10,751,155 B2
(45) Date of Patent: Aug. 25, 2020

(54) COSMETIC IMPLANT FOR EYE ENLARGING SURGERY AND SURGICAL INSTRUMENTS AND SURGICAL PROCEDURES USING THE SAME

(71) Applicant: Dong Ho Lee, Seoul (KR)

(72) Inventor: Dong Ho Lee, Seoul (KR)

( * ) Notice: Subject to any disclaimer, the term of this patent is extended or adjusted under 35 U.S.C. 154(b) by 0 days.

(21) Appl. No.: 16/081,892

(22) PCT Filed: Mar. 23, 2017

(86) PCT No.: PCT/KR2017/003094
§ 371 (c)(1),
(2) Date: Aug. 31, 2018

(87) PCT Pub. No.: WO2018/079952
PCT Pub. Date: May 3, 2018

(65) Prior Publication Data
US 2019/0192269 A1    Jun. 27, 2019

(30) Foreign Application Priority Data

Oct. 27, 2016 (KR) .......................... 10-2016-0141414

(51) Int. Cl.
*A61F 2/00* (2006.01)
*A61F 2/14* (2006.01)
*A61F 9/007* (2006.01)

(52) U.S. Cl.
CPC ............ *A61F 2/0059* (2013.01); *A61F 2/142* (2013.01); *A61F 2/148* (2013.01); *A61F 9/007* (2013.01); *A61F 2230/0065* (2013.01)

(58) Field of Classification Search
CPC .. A61F 2/0059; A61F 2/14; A61F 2/141–147; A61F 2/1605;
(Continued)

(56) References Cited

U.S. PATENT DOCUMENTS 5,372,580 A   12/1994 Simon et al.
6,565,584 B1   5/2003 Mathis et al.
(Continued)

FOREIGN PATENT DOCUMENTS

CN        2145595 Y    11/1993
CN     102970942 A     3/2013
(Continued)

OTHER PUBLICATIONS

Webster, Noah. "Adhere," American Dictionary of the English Language (http://webstersdictionary1828.com/Dictionary/adhere) Year: 1828).*

*Primary Examiner* — Brian A Dukert
*Assistant Examiner* — Amanda M Barkan
(74) *Attorney, Agent, or Firm* — TIPS Group

(57) ABSTRACT

An eye enlargement implant and a method of performing a cosmetic procedure for the beauty of eyes, which is capable of being inserted into the eyes so as to make the eye look crisper and bigger, and being removed when it is not necessary without causing eye inflammation and without having to be replaced, the implant including a ring-shaped body which is inserted between a sclera and a conjunctiva of an eyeball having an inner diameter portion having at least a size enough to surround an outer periphery of the cornea, and an outer diameter portion having a width size of 0.8 to 1.2 mm so as to cover a white portion and having a maximum thickness of 0.05 to 0.20 mm at the center portion, where the ring-shaped body has flexibility and a predetermined color which is similar to that of the iris.

4 Claims, 13 Drawing Sheets

(58) Field of Classification Search
CPC ............ A61F 2230/0065; A61F 9/0017; A61F 9/0008; A61F 9/007; A61F 9/00736; B29D 11/023
See application file for complete search history.

(56) References Cited

U.S. PATENT DOCUMENTS

| | | | |
|---|---|---|---|
| 8,162,953 B2 * | 4/2012 | Dishler | ............... A61F 2/148 606/107 |
| 2004/0143324 A1 | 7/2004 | Melles | |
| 2017/0319330 A1 * | 11/2017 | Guerreschi | ........... A61F 2/1451 |

FOREIGN PATENT DOCUMENTS

| | | |
|---|---|---|
| JP | 2013-524994 A | 6/2013 |
| KR | 10-0541058 B1 | 1/2006 |
| KR | 10-2015-0080488 A | 7/2015 |
| KR | 10-2016-0108612 A | 9/2016 |
| KR | 10-1713055 B1 | 3/2017 |

\* cited by examiner

[FIG 1]
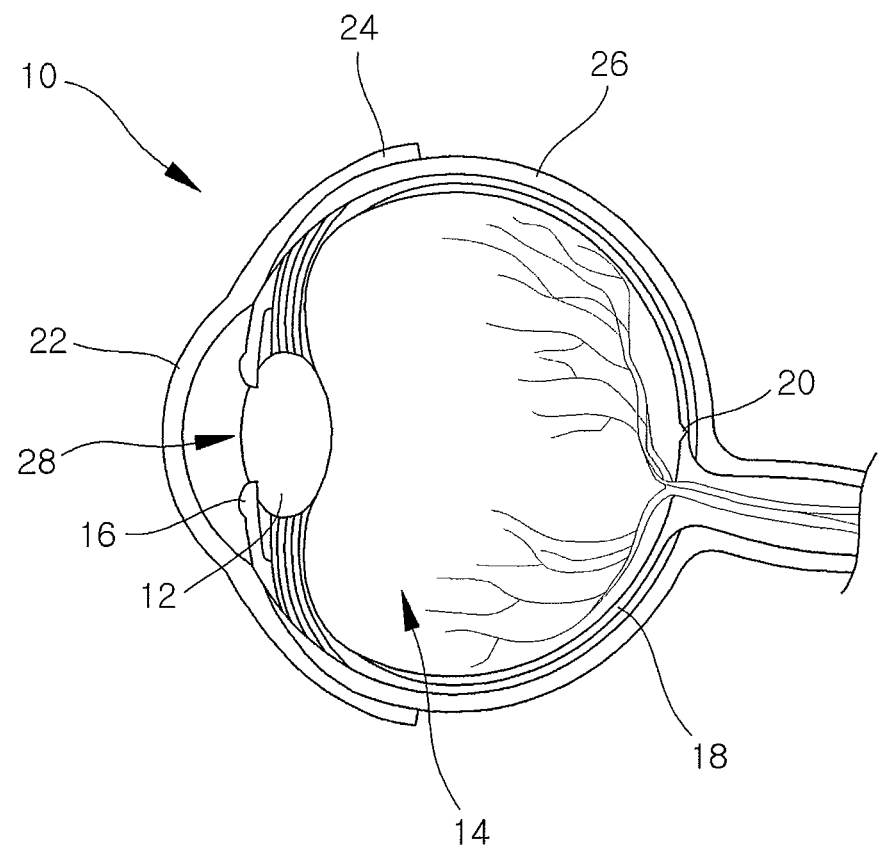
[FIG. 2]
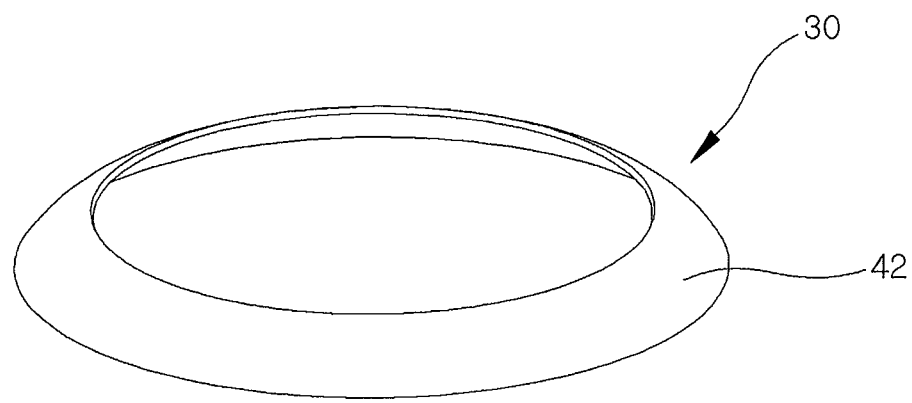

[FIG. 3]
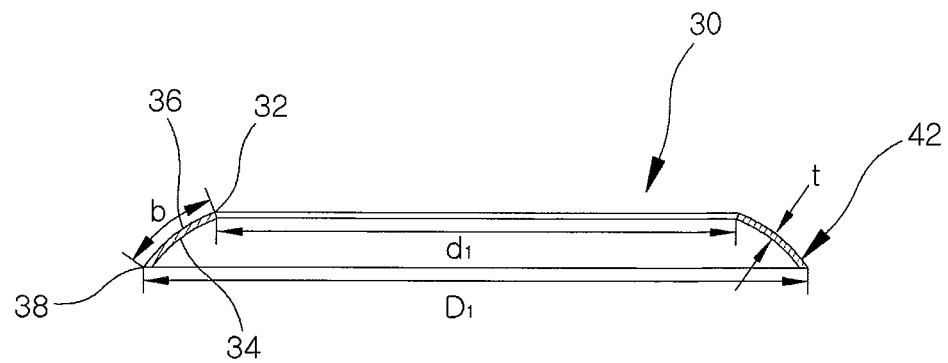
[FIG. 4]
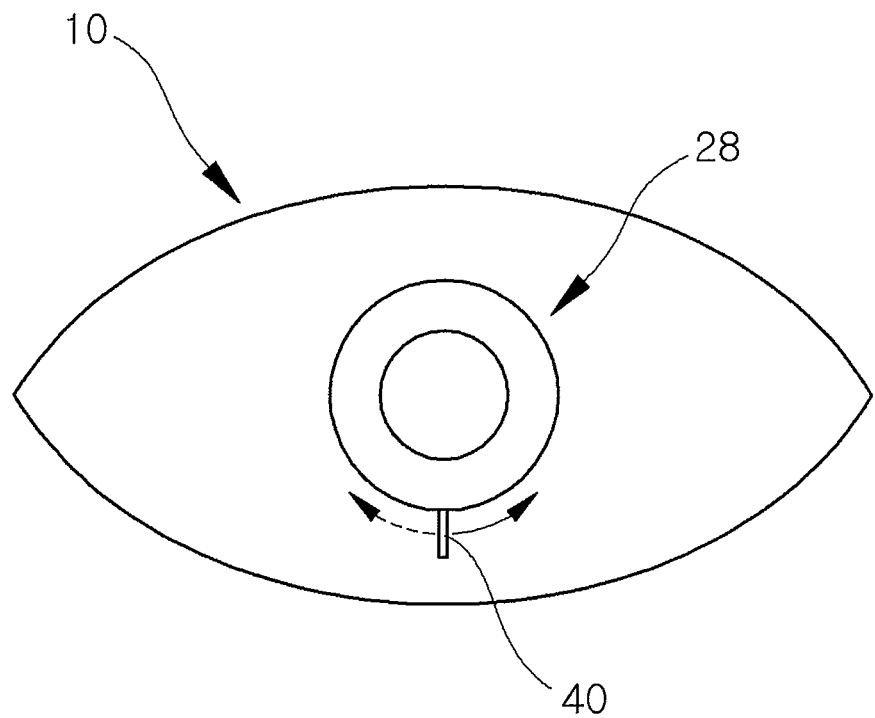

[FIG. 5]
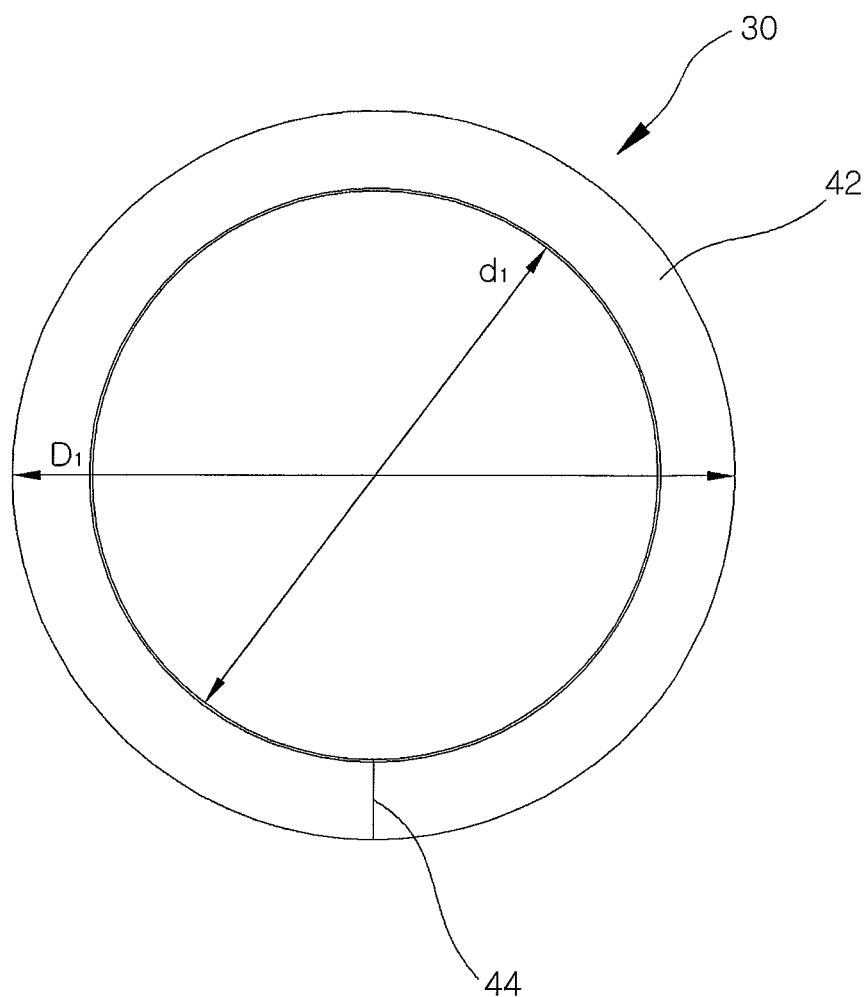

[FIG. 6]
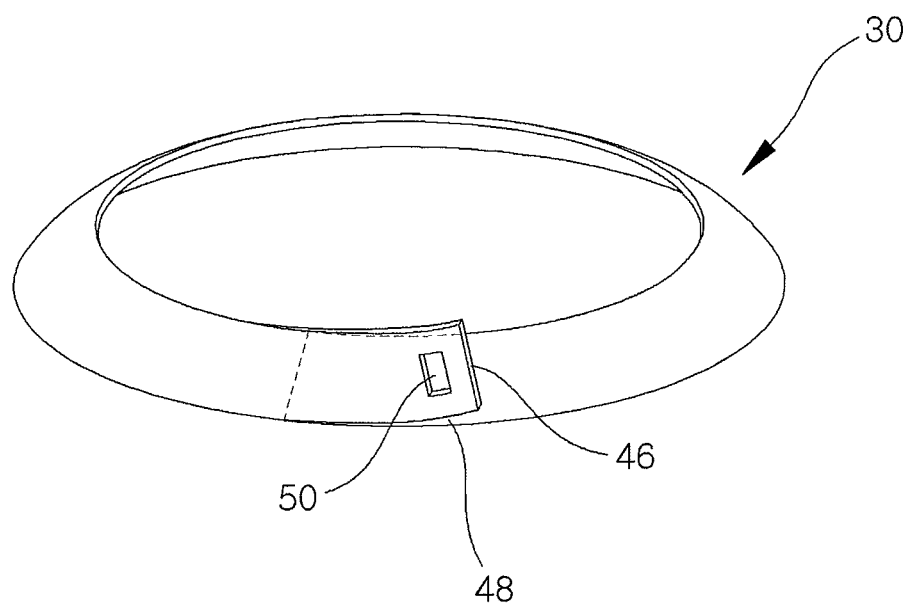

[FIG. 7]
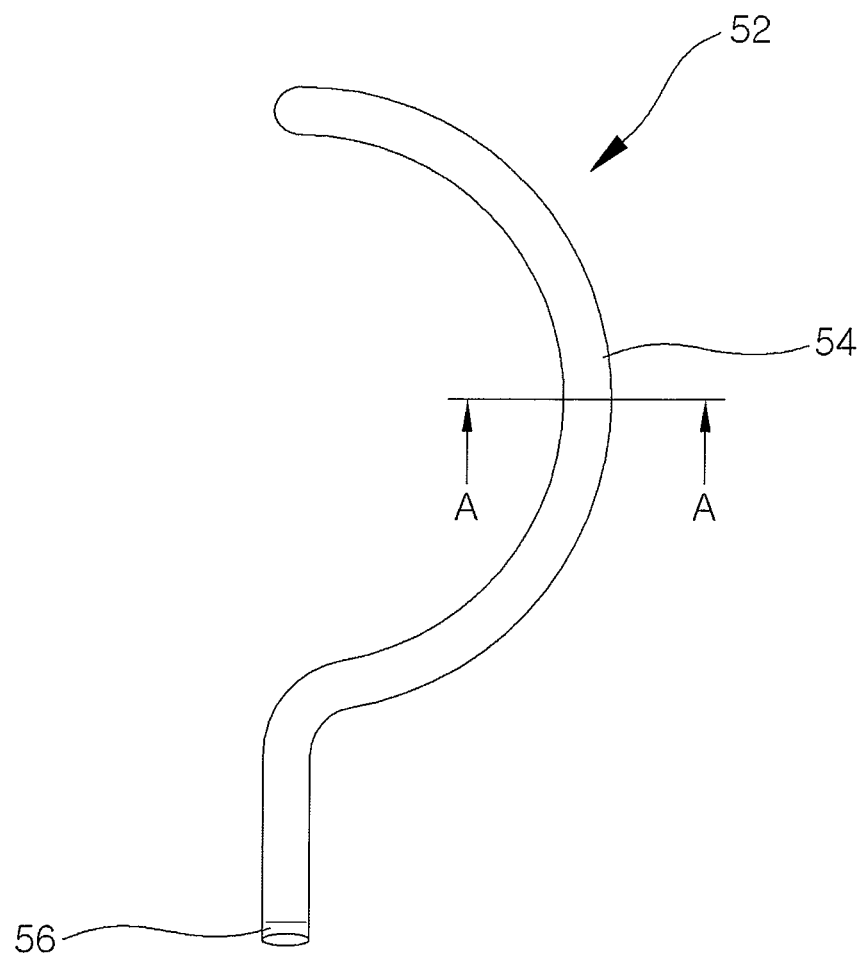

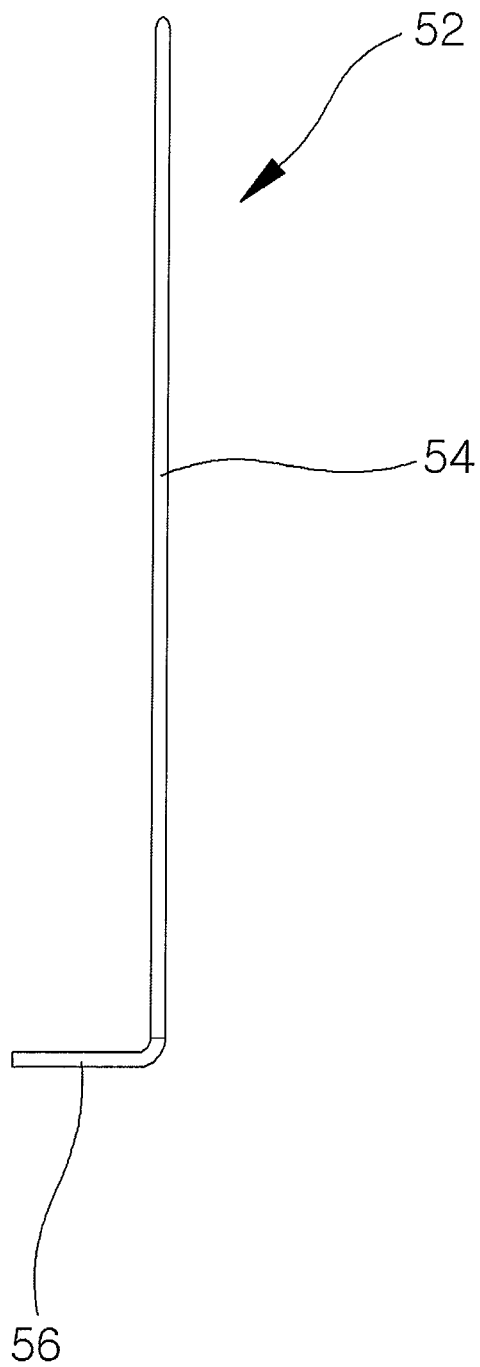
[FIG. 8]

[FIG. 9]
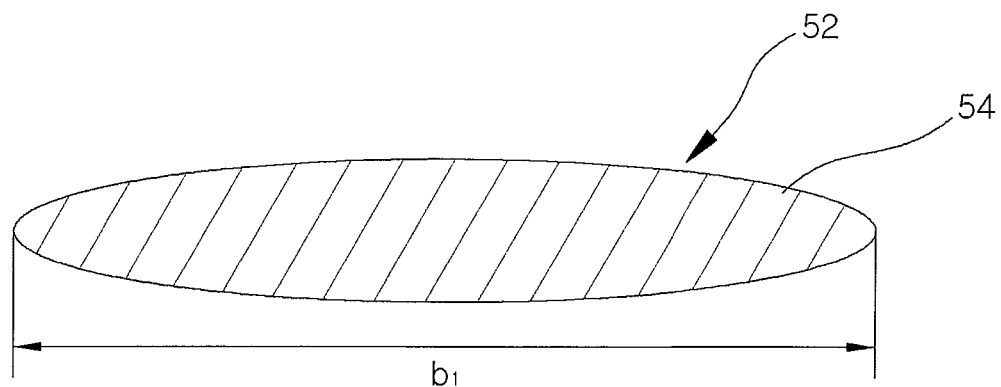

[FIG. 10]
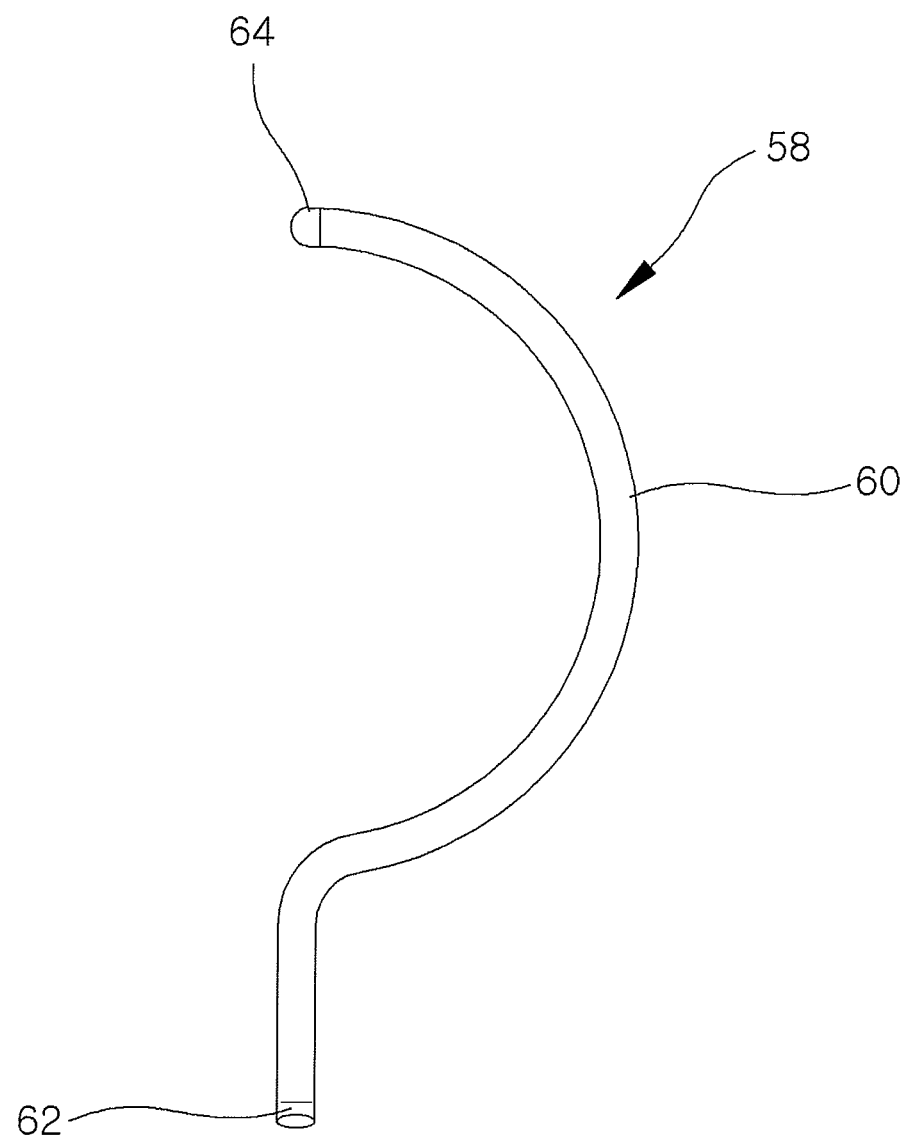

[FIG. 11]
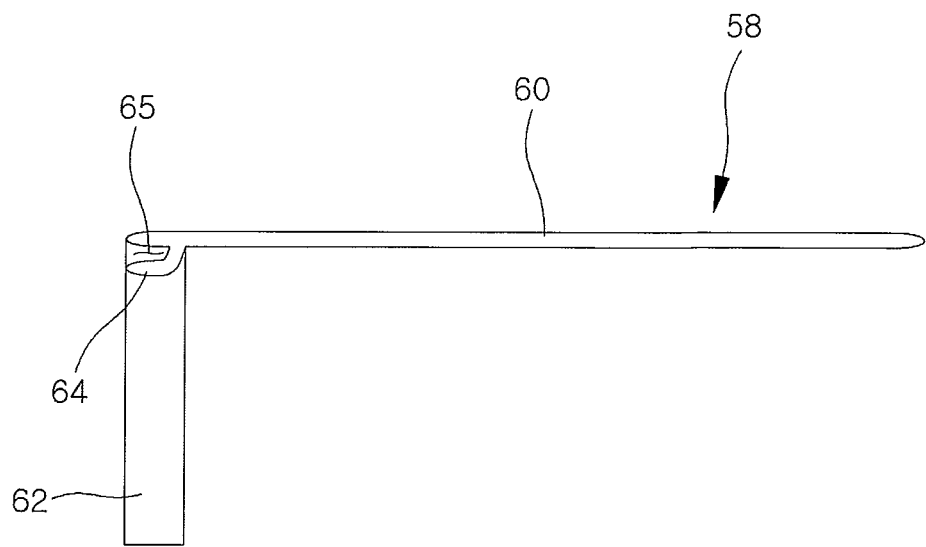

[FIG. 12]
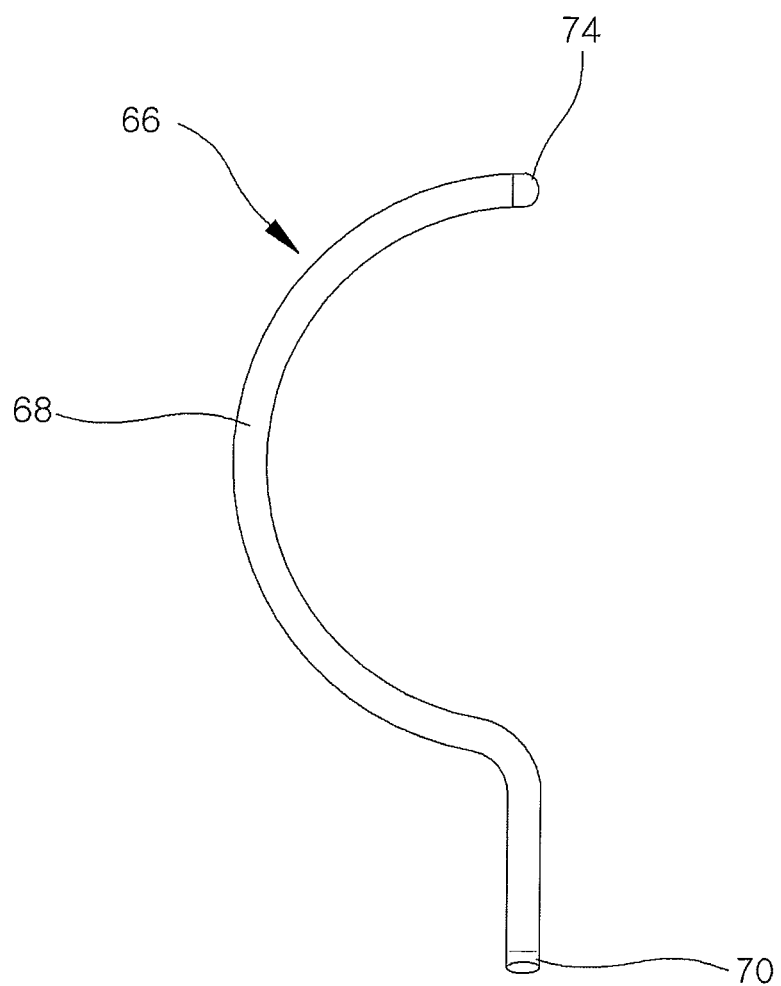

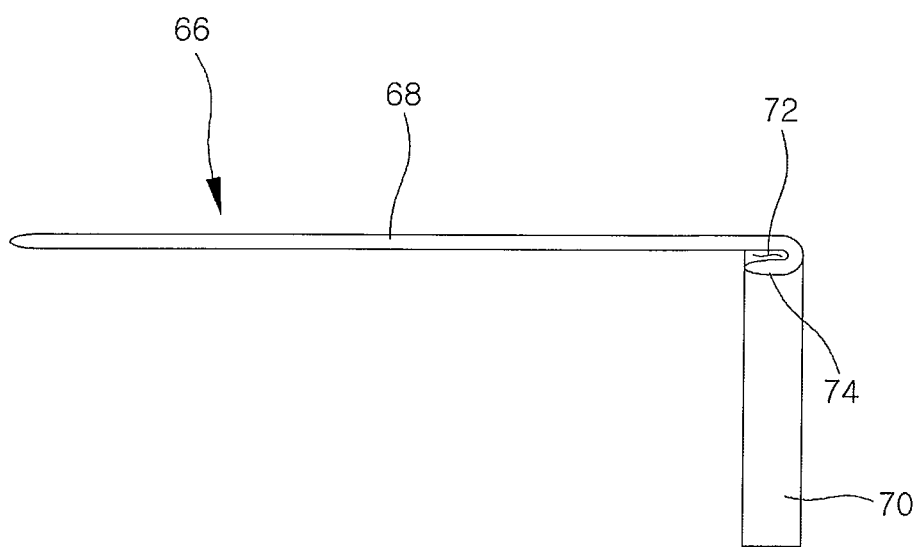
[FIG. 13]

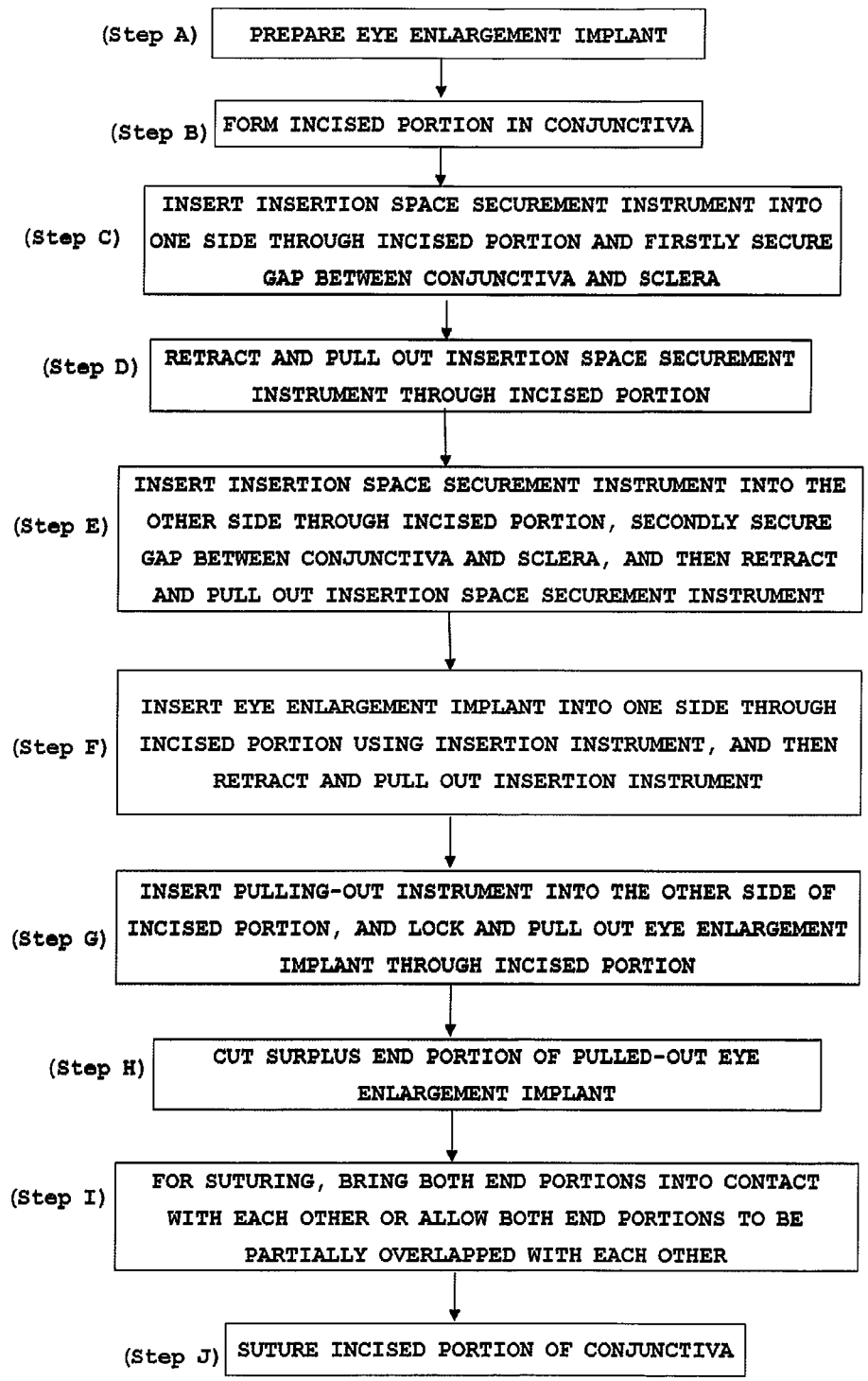

[FIG. 15]
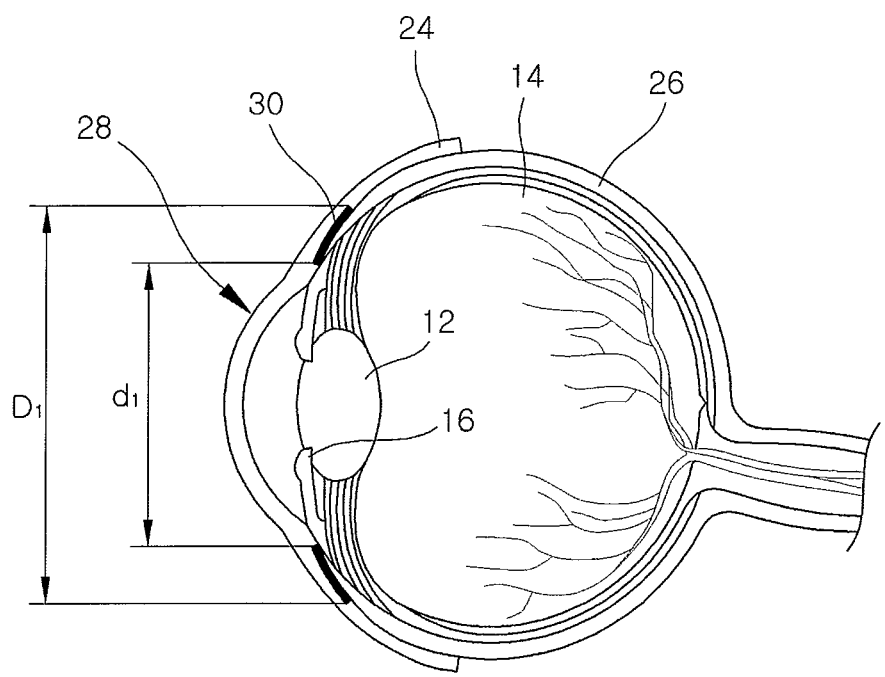

COSMETIC IMPLANT FOR EYE ENLARGING SURGERY AND SURGICAL INSTRUMENTS AND SURGICAL PROCEDURES USING THE SAME

CROSS REFERENCE TO RELATED APPLICATION(S)

This application is a U.S. National Phase Application under 37 C.F.R. § 371 of PCT/KR2017/003094, filed Mar. 23, 2017, and claims the priority of Korean Patent Application No. 10-2016-0141414, field Oct. 27, 2016, both of which are incorporated herein by reference.

TECHNICAL FIELD

The present invention relates to a cosmetic implant placed around cornea for making eye look bigger, a method of performing a cosmetic surgical procedure using the implant, and surgical instruments used in the cosmetic surgical procedure for making eye look bigger.

BACKGROUND ART

A center part of an eyeball, which has a circular shape and looks black or brown in Asian or blue in caucasian, is called an apple of the eye or simply eye, and is also referred to as a region commonly including the iris and pupil. In the present invention, eye means this central part of eyeball which has color according to the color of iris. Eye enlargement means making this center part, eye, look bigger by inserting eye enlargement implant around cornea.

The pupil is an open part at a center of the iris (diaphragm). Light, which has passed through a cornea, passes sequentially through the pupil and through a crystalline lens, and then is refracted to reach a retina. Due to relaxation and contraction actions of muscles in the iris, the pupil shrinks in a light place and is enlarged in a dark place. As a result, light is regulated so as to enter the retina in an appropriate amount. However, if a brain, especially a midbrain is injured because of severe stroke, head injury, or cancer etc, such a regulation ability is deteriorated or disappeared.

For this reason, when a patient is unconscious, neurology/neurosurgery/emergency medicine doctors and nurses always look at the patient's pupils with pen light. With regard to the original pupil, which is composed of the empty space, all people on the earth have the same color, which is black. In contrast, the iris varies depending on races, which is one characteristic point in terms of distinguishing races from each other.

Actual color of the pupil is transparent, but the pupil looks black since the retina hardly reflects light entering the eyeball. However, in a case in which intense light is shot at the pupil directly and instantaneously, the pupil looks red since the red color of the inner wall of the eyeball becomes visible through the pupil (looks red because blood vessels pass through the wall), which is the cause of the red eye effect when a flash is lit up.

The color of the iris is different for each person, especially, for each race, and is largely divided into blue, brown, and dark brown. The iris is the colored part that has a melanin pigment, representing the color of the eye. The color of the eye is determined according to an amount and distribution of the melanin pigment. When the amount of melanin pigment is small, the iris looks blue, when the amount is large, the iris looks brown, when the pigment is deficient, the eye looks red, which is the color of the blood vessel, and when the amount of the melanin pigment is large, the eye looks dark brown.

Since the color around the eye that lies at the center of the eye (black, in a case of Asian) is usually white (the part is usually referred to as 'white' or sclera), the distinctive contrast of colors reveals the size of the eye noticeably, and the crisp, big eyes are the target of envy as a measure of women's beauty.

For this reason, recently, circle lenses have been widely worn to make the eye look crisper and bigger.

Circle lenses are one type of color lenses, and mainly have a black color put on edges thereof for beauty, thereby making the eye look bigger when the lenses are worn on. However, the circle lenses have a relatively large thickness due to the pigment, which leads to low oxygen permeability, and the resulting lowered supply of oxygen may be one cause of eye inflammation. The inflammation may cause vision loss or some other side effects, for example, a side effect that the eye looks smaller by blurring a boundary between the white and the dark eye.

As described above, the circle lenses with color put on the edges thereof so as to make the eye look bigger are mainly used for cosmetic purpose, rather than for vision correction. However, if the circle lenses are used indiscriminately without the doctor's prescription, the lenses may cause eye diseases. In addition, cosmetic contact lenses have some disadvantages such as a relatively lower oxygen permeability due to a coloring agent that blocks fine holes in a lens surface, than the ordinary contact lenses for vision correction. Further, the lens has a rough and irregular surface, thus to give a stimulus to the eyes and increase contact area and frequency between the bacteria and the lenses, thereby resulting in a good environment for the bacteria to reproduce. Therefore, when the circle lenses are put on the eyes for beauty for a long time, side effects such as neovascularization, keratitis, corneal ulceration, corneal edema, and the like may occur.

Among them, neovascularization may have an effect of making the eyes look rather smaller. This is because, when wearing the cosmetic circle lenses for a long time, the lowered oxygen permeability may cause hypoxia in the cornea. Thereby, neovascularization may occur on the edge of the cornea and may spread up to the vicinity of the cornea so that the edge of the cornea looks whitish and cloudy, which may make the eye look smaller. Therefore, there is a situation that desperately needs an alternative to the circle lenses, which is capable of accomplishing the cosmetic purpose without harming the health of the eye.

SUMMARY OF INVENTION

Problems to be Solved by Invention

In consideration of the above-mentioned circumstances, it is an object of the present invention to provide an eye enlargement implant for beauty of eyes capable of being inserted into the sub-conjunctival space around cornea so as to make the eye look crisper and bigger to maximize the cosmetic effect, and being removed when it is not necessary, without causing eye inflammation and without having to be replaced.

Another object of the present invention is to provide surgical procedures of performing a cosmetic procedure using the eye enlargement implant capable of safely inserting the eye enlargement implant for beauty of the eyes.

Further, another object of the present invention is to provide an insertion instrument for the eye enlargement implant into the eye, which is capable of accurately and safely inserting the eye enlargement implant for beauty of the eyes into the eye, and an insertion space securement instrument, which is capable of securing the insertion space for the insertion instrument in advance.

Means for Solving Problems

In order to achieve the above-described objects, according to one aspect of the present invention, there is provided an eye enlargement implant for beauty of eyes, including a ring-shaped body which is inserted between a sclera and a conjunctiva of an eyeball, wherein the ring-shaped body has an inner diameter portion having at least a size enough to surround an outer periphery of a cornea, and an outer diameter portion having a width size of 0.8 to 1. 2 mm so as to cover a white portion with a predetermined width and having a maximum thickness of 0.05 to 0.20 mm at a center portion in a cross section taken in a width direction thereof, the ring-shaped body is made of a material having flexibility and the same color as that of the iris, and has a cutting part for facilitating insertion into the sub-conjunctival space, and both end portions of the ring-shaped body around the cutting part are adhered or sewn with each other after insertion into the eyeball. In addition, the ring-shaped body may be made by including at least one material selected from a silicone derivative, polyamide, polyhydroxyethyl methacrylate (PHEMA), polyvinyl pyrrolidone (PVP), polyvinylidene difluoride, methyl methacrylate-acrylic acid polymer (RPG), cellulose acetate butyrate (CAB) and polymethyl methacrylate (PMMA).

According to an embodiment of the present invention, the ring-shaped body may have a hooking hole formed in one end portion thereof based on the cutting part whose both end portions are adhered or sewn with each other, into which a hook is inserted and locked so as to pull and move the ring-shaped body.

According to an embodiment of the present invention, at least one end portion of the ring-shaped body may extend so as to overlap with the other end portion thereof based on the cutting part, an extra overlapping portion may be cut after insertion into the eyeball in a ring shape, and both end portions of the ring-shaped body may be adhered and sewn with each other.

According to another aspect of the present invention, there is provided an insertion space securement instrument of the eye enlargement implant into the eye, wherein the securement instrument is made of a metal alloy material, a plastic material or a silicone material for a surgical instrument, and the securement instrument includes: a semicircular ring-shaped instrument which is inserted through an incised portion formed in a conjunctiva and secures an insertion space between the conjunctive and a sclera of the eyeball in advance so as to insert the eye enlargement implant; and a grip formed at one end portion of the semicircular ring-shaped instrument, wherein the insertion space securement instrument has a body formed in a question mark shape as a whole, and the body has a cross section of an elliptical shape.

In addition, according to another aspect of the present invention, there is provided an insertion instrument for inserting the eye enlargement implant according to the present invention into an eyeball, wherein the insertion instrument is made of a metal alloy material, a plastic material or a silicone material for a surgical instrument, and is inserted into the eyeball in one direction thereof through an incised portion formed in a conjunctiva, the insertion instrument includes: a semicircular insertion instrument body which is inserted along a gap formed between the conjunctiva and a sclera so as to surround an outer periphery of a cornea; a U-shaped hook which is opened toward an outer end so as to be locked to an edge portion of a hooking hole formed in one end portion of the eye enlargement implant at a tip portion of the semicircular insertion instrument body; and a grip formed at the other end portion of the insertion instrument body facing the hook, and the insertion instrument is configured to lock the hook to the edge portion of the hooking hole of the eye enlargement implant to push the eye enlargement implant in one direction through the incised portion, and when the tip portion of the eye enlargement implant reaches a side opposite to the incised portion, to retract and collect the hook with the eye enlargement implant being left.

Further, according to another aspect of the present invention, there is provided an insertion instrument for inserting the eye enlargement implant according to the present invention into an eyeball, wherein the insertion instrument is made of a metal alloy material, a plastic material or a silicone material for a surgical instrument, and is used to pull out the eye enlargement implant inserted into the eyeball in one direction thereof through an incised portion formed in a conjunctiva toward the other direction, the insertion instrument includes: a semicircular pulling-out instrument body which is inserted along a gap formed between the conjunctiva and a sclera so as to surround an outer periphery of a cornea; a U-shaped hook which is opened toward an inner end so as to be locked to an edge portion of a hooking hole of the eye enlargement implant at a tip portion of the semicircular pulling-out instrument body; and a grip formed at the other end portion of the pulling out section body facing the hook, and the insertion instrument is configured to insert the hook through the incised portion in a direction opposite to a direction in which the eye enlargement implant inserted in the eyeball enters, lock the hook to the edge portion of the hooking hole formed in the tip portion of the eye enlargement implant, and pull out the hook toward the incised portion.

Furthermore, according to another aspect of the present invention, there is provided a method of performing a cosmetic procedure using the eye enlargement implant according to present invention including: incising a conjunctiva so as to have a predetermined width in a radial direction of a cornea from a position of an outer periphery of the cornea; inserting one end portion of the eye enlargement implant of which one side is cut and which has an inner diameter to surround the outer periphery of the cornea, between a sclera and the conjunctiva through the incised portion; turning the inserted end portion around the outer periphery of the cornea and then pulling out the end portion through the incised portion; suturing both end portions of the eye enlargement implant; and suturing the incised portion of the conjunctiva.

According to a preferred embodiment of the present invention, the method may further include securing a space into which the eye enlargement implant is inserted between the conjunctive and the sclera by inserting an insertion space securement instrument through the incised portion in advance before inserting the eye enlargement implant.

According to an embodiment of the present invention, the eye enlargement implant may be inserted so as to surround the outer periphery of the cornea by an instrument for guiding the implant into the eyeball and pulling out the implant.

According to an embodiment of the present invention, one end portion of the eye enlargement implant may extend beyond the other end portion, a surplus portion may be cut after the pulling out, and both end portions thereof may be sutured so as to be brought into contact face to face or be partially overlapped with each other.

Advantageous Effects

As described above, according to the present invention, the ring-shaped eye enlargement implant having the color similar to that of the iris is inserted between the conjunctiva and the sclera so as to surround the outer periphery of the cornea, which makes the eye look crisper and bigger, and thus enhances the cosmetic effect of the eyes. In addition, through the eye enlargement implant described above, it is possible to prevent a damage to the cornea and the conjunctiva caused by ocular drying and frictional contact with lenses, which may occur due to the lowered oxygen permeability at the time of wearing the conventional color lenses. Further, since a single procedure does not incur additional costs, using the eye enlargement implant is more economical than wearing the circle lenses which are relatively expensive as a one-time consumable. Furthermore, it is possible to remove the eye enlargement implant when it is not necessary, and there is no probability of damaging the eye by the structure that does not cover the cornea.

BRIEF DESCRIPTION OF DRAWINGS

FIG. 1 is a view illustrating a structure of an eyeball.

FIG. 2 is a perspective view illustrating an eye enlargement implant according to the present invention.

FIG. 3 is a front sectional view illustrating the eye enlargement implant according to the present invention.

FIG. 4 is a view illustrating a part of an incised conjunctiva of an eyeball before inserting the eye enlargement implant according to the present invention.

FIG. 5 is a plan view illustrating the eye enlargement implant according to the present invention, with a part of a ring-shaped body being cut.

FIG. 6 is a view illustrating a shape of the eye enlargement implant according to a preferred embodiment of the present invention, with one end portion extending beyond the other end portion in a predetermined length.

FIG. 7 is a front view illustrating a securement instrument used for securing an insertion space between a conjunctive and a sclera in advance so as to insert the eye enlargement implant according to the present invention.

FIG. 8 is a side view illustrating an insertion space securement instrument illustrated in FIG. 7.

FIG. 9 is a cross-sectional view taken on line A-A of the insertion space securement instrument in FIG. 7.

FIG. 10 is a front view illustrating an insertion instrument for inserting the eye enlargement implant according to the present invention into the eyeball.

FIG. 11 is a side view of the insertion instrument illustrated in FIG. 10.

FIG. 12 is a front view illustrating a pull-out instrument for pulling out the eye enlargement implant in a state in which a part of the body thereof is inserted into the eyeball through the insertion instrument of FIG. 10 into an incised portion formed in the conjunctiva.

FIG. 13 is a side view illustrating the pull-out instrument illustrated in FIG. 12.

FIG. 14 is a flowchart illustrating a cosmetic procedure method of inserting the eye enlargement implant according to the present invention in steps.

FIG. 15 is a cross-sectional view illustrating an eyeball with the eye enlargement implant according to the present invention being inserted therein.

MODE FOR CARRYING OUT INVENTION

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these exemplary embodiments are provided so that this disclosure is thorough, and will fully convey the scope of the invention to those skilled in the art. The drawings are not necessarily to scale, and in some instances, proportions may have been exaggerated in order to clearly illustrate features of the embodiments. Throughout the disclosure, like reference numerals refer to like parts throughout the various figures and embodiments of the present invention. In addition, in the embodiments of the present invention, the publicly known functions and configurations which are judged to be able to make the purport of the present invention unnecessarily obscure will not be described.

Further, in the definition of terms, an eye refers to the part of an eyeball including an iris and pupil that looks black in Asian, and the part that looks whitish around the eye refers to white.

FIG. 1 illustrates a human eyeball structure. The eyeball 10 includes a crystalline lens 12 that has a transparent structure with a convex lens shape on both sides inside an eyeball and allows a thickness and a curvature to be adjusted so as to collect light as the light passes there through and cause an image to be formed on a retina, and a vitreous body 14 located behind the crystalline lens. The eyeball 10 further includes an iris 16 which is located in front of the crystalline lens 12 and adjusts an amount of light entering the eyeball by controlling a size of the pupil through contraction and relaxation of a donut-shaped membrane positioned around the pupil, a retina 18 which is located behind vitreous body 14 and allows an image to be formed thereon, a macula 20, a cornea 22 that covers the front of the iris 16 so as to protect the same, a conjunctiva 24, and a sclera 26. In addition, the crystalline lens 12 and the iris 16 are held at a center of the anterior eyeball by zonule and ciliary body. A pupil 28 is located in front of the crystalline lens 12 and the iris 16, and functions so as to receive light from an outside and transmit visual information formed on the retina to a brain through optic nerves.

As described above, the sclera 26 is placed on a surface of the eyeball 10, and the conjunctiva 24 surrounds an outer side of the sclera 26, such that the conjunctiva 24 and the cornea 22 forms outer walls of the eyeball 10.

FIG. 2 is a perspective view illustrating an eye enlargement implant according to the present invention, which is denoted by reference numeral 30.

The eye enlargement implant 30 has an inner edge portion 32 surrounding an outer periphery of the cornea 22 in a circle, a lower curved portion 34 and an upper curved portion 36, which extends in close contact with the surface of the sclera 26 starting from the inner edge portion 32, and an outer edge portion 38 having the largest diameter as illustrated in a front sectional view of FIG. 3. The inner edge portion 32 has a diameter d1 corresponding to a size of the cornea of a human being, that is, of about 10 to 12 mm. The eye enlargement implant 30 has a maximum thickness t of 0.05 to 0.20 mm, preferably 0.08 to 0.12 mm, and more preferably 0.1 mm, and a width b of about 0.8 to 1.2 mm. The outer edge portion has a diameter D1 of about 12 to 14 mm, and a cross section of a ring shape formed in a nail end or crescent shape. In the drawings, the outer edge portion is illustrated with a constant thickness for the sake of convenience, but may have a cross-sectional shape whose thickness is gradually reduced toward an inner end portion and an outer end portion from the maximum thickness t at the center of a body of the eye enlargement implant.

The body of the eye enlargement implant 30 is made of a medical material that can be safely used for medical purposes, for example, any one material selected from a silicone derivative such as silicon rubber or silicon hydrogel and polydimethylsiloxane (PDMS), a polyamide, a polyhydroxyethyl methacrylate (PHEMA), polyvinyl pyrrolidone (PVP), polyvinylidene difluoride, methyl methacrylate-acrylic acid polymer (RPG), cellulose acetate butylate (CAB), and polymethyl methacrylate (PMMA). In addition, the body of the eye enlargement implant 30 is colored according to the color of the iris of an individual or the color which an individual prefers, and is colored so as to exhibit a predetermined color with a pigment having, for example, black, brown, gray, green, or blue color, or a combination of two or more of these colors (but, it is not limited to the above-described colors).

The ring-shaped eye enlargement implant 30 is inserted between the conjunctiva 24 and the sclera 26 to cover the white with being inserted. Therefore, when other people look at the eye, the eye looks enlarged to the outer diameter D1 of the eye enlargement implant 30.

To insert the ring-shaped eye enlargement implant 30 between the conjunctiva 24 and the sclera 26, it is necessary for a part of the conjunctiva 24 to be incised. As illustrated in FIG. 4, a part of the conjunctive 24 surrounding the surface of the eyeball is incised along a line in a direction in which the radius of the iris 16 expands using a surgical instrument to form an incised portion 40 so as to have a predetermined width, and the eye enlargement implant 30 is inserted through the incised portion 40. In this case, the incised portion 40 is incised slightly larger than the width b of the eye enlargement implant 30.

The eye enlargement implant 30 has a cutting part 44 (or suturing part) formed by cutting a ring-shaped body 42 so as to allow the eye enlargement implant 30 to be inserted into the eyeball through the incised portion 40. Both end portions of the eye enlargement implant 30 are separated from each other based on the cutting part 44 before insertion into the eyeball, and after completing insertion into the eyeball, are sutured to form the suturing part, which will be described below.

FIG. 6 is a view illustrating a shape of the eye enlargement implant according to a preferred embodiment of the present invention before performing a procedure, wherein one end portion 46 is longer in a length than the other end portion 48 such that both end portions of the eye enlargement implant are overlapped with each other. The eye enlargement implant has a hooking hole 50 formed in the vicinity of the one end portion, into which an insertion instrument and a pulling instrument to be described below is inserted by hooking and pushing so as to move a position thereof or pull.

FIG. 7 illustrates an insertion space securement instrument 52 for securing an insertion space necessary to insert the eye enlargement implant 30 between the conjunctiva 24 and the sclera 26 of the eyeball. The securement instrument has a question-mark shape as a whole, and includes a semicircular ring-shaped instrument 54, and a grip 56 which is bent and extends in a direction about perpendicular to a tangential direction on one end portion side of the semicircular ring-shaped instrument 54. It is preferable that the grip 56 is bent in an L shape so that a doctor who performs the procedure can easily hold it and do the performance. The grip has a cross section of a flat streamlined or convex lens shape as illustrated in FIG. 9, and is designed so as to have a width b1 similar to the width b of the eye enlargement implant 30.

The eyeball has the conjunctiva 24 and the sclera 26 in closely contact with each other under a normal condition. Therefore, in order to insert the eye enlargement implant into the eyeball, it is necessary to secure the insertion space in advance. For this purpose, the insertion space securement instrument 52 is used. The insertion space securement instrument 52 is pushed into the eyeball in a counterclockwise (or clockwise) direction between the conjunctiva 24 and the sclera 26 starting from a tip of the semicircular ring-shaped instrument 54 through the incised portion 40 formed in the conjunctiva 24. When the tip thereof enters a gap between the conjunctiva and the sclera, the tip is smoothly pushed and gradually inserted in a circular motion around the outer periphery of the cornea 22 using the grip 56, and thus the semicircular ring-shaped instrument 54 stretches the conjunctive 24 with good stretchability, and as a result a gap is formed between the conjunctiva and the sclera 26. When the space securing operation of the half of the eyeball is completed, the insertion space securement instrument 52 is retracted in a direction opposite to a direction in which the insertion space securement instrument 52 enters, and is pulled out through the incised portion. Then, other insertion space securement instrument 52, which is symmetrical with the securement instrument, or the securement instrument 52, which is pulled out and turned over, is inserted through the incised portion 40 in the direction opposite to the above-mentioned direction, that is, a clockwise (or counterclockwise) direction starting from the ring-shaped instrument 54, thereby securing the remaining half of the insertion space (gap).

The above-described insertion space securement instrument 52 is made of a metal alloy material, a plastic material or a silicone material for a surgical instrument, and is preferably subjected to a round process on the tip portion thereof so as not to be angled, thus to prevent an injure during the insertion.

FIGS. 10 and 11 are a front view and a plan view, respectively, illustrating an insertion instrument 58 for guiding insertion of the eye enlargement implant 30 between the conjunctive and the sclera when the insertion space for inserting the eye enlargement implant 30 is secured by the insertion space securement instrument 52. The insertion instrument 58 has a question-mark shape as a whole when viewing from a front, similar to the insertion space securement instrument 52 illustrated in FIG. 7, and is made of a metal alloy material, a plastic material or a silicone material for a surgical instrument.

The insertion instrument 58 includes a semicircular insertion instrument body 60 having a flat and thin elliptical cross section, a grip 62 which is bent and extends in a direction perpendicular to the tangential direction at one end of the semicircular insertion instrument body 60, and a hook 64 which is provided at the tip of the semicircular insertion instrument body 60 and has an opening groove 65 which is opened outward so that the hook is locked to an edge portion of the hooking hole 50 of the eye enlargement implant 30. It is preferable that the grip 60 is formed in an L shape bent at any angle so that a practitioner (doctor) can easily hold and grip it.

FIG. 12 is a front view illustrating a pulling-out instrument 66 that forms a pair with the insertion instrument 58 (the pulling-out instrument is also an instrument which is used for inserting the eye enlargement implant into the eyeball, such that when it is necessary to distinguish the pulling-out instrument from the insertion instrument for the purpose of explanation, the pulling-out instrument is described as the pulling-out instrument itself, and when it is not necessary to distinguish, for example, when the pulling-out instrument is defined in an independent claim separate from the insertion instrument 58, it is described as the insertion instrument). The pulling-out instrument 66 also has a question-mark shape as a whole, and is made of a metal alloy material, a plastic material, or a silicone material for a surgical instrument. The pulling-out instrument 66 includes a semicircular pulling-out instrument body 68 having a flat and thin elliptical cross section, a grip 70 which is bent and extends in a direction perpendicular to the tangential direction at one end of the semicircular pulling-out instrument body 68, and a hook 74 which is provided at the tip of the semicircular pulling-out instrument body 68 and has an opening groove 72 which is opened toward the body so that the hook is locked to the edge portion of the hooking hole 50 of the eye enlargement implant 30. It is preferable that the grip 70 is formed in an L shape so that a practitioner (doctor) can easily hold and grip it.

The pulling-out instrument 66 is an instrument which is to be used after the insertion instrument 58 guides the tip of the eye enlargement implant 30 to a position of 180 degrees with respect to the incised portion 40, and then is retracted and pulled out through the incised portion 40. The pulling-out instrument 66 is inserted through the incised portion 40 in a direction opposite to a direction in which the inserting portion 58 is inserted, for example, if the insertion instrument 58 is inserted in the counter-clockwise direction, the pulling-out instrument 66 is inserted in the clockwise direction opposite thereto. When the pulling-out instrument 66 is inserted and the hook 74 at the tip thereof reaches the 180-degree position of the eyeball, after the hook 74 is locked to the edge portion of the hooking hole 50 at the tip of the eye enlargement implant 30 which has been inserted to that position and has been in a standby state, the pulling-out instrument 66 is drawn in a circular motion and pulled out of the eyeball (the insertion instrument 58 pushes the eye enlargement implant 30 while the pulling-out instrument 66 pulls out the eye enlargement implant 30). By doing so, as the tip of the eye enlargement implant 30 is pulled by the pulling-out instrument 66, the tip is turned around the outer periphery of the cornea and pulled out through the incised portion 40. When the tip is pulled out as described above, the eye enlargement implant 30 is inserted in a ring shape so as to surround the periphery of the cornea by 360 degrees, and thus the eye enlargement implant 30 is positioned between the conjunctiva and the sclera.

Hereinafter, a method of performing a cosmetic procedure in which the eye enlargement implant 30 according to the present invention is inserted into an eyeball will be described in steps with reference to a flowchart in FIG. 14.

First, a ring-shaped eye enlargement implant 30 is prepared (Step A). When various examinations of the eyeball are completed, in order to insert the eye enlargement implant 30, a practitioner (doctor) incises only the conjunctiva 24 which is formed as an outer layer of the eyeball, starting from an outer boundary of a cornea or the slightly inner place thereof, and extending in a straight line with a predetermined width, for example, a size slightly greater than the width b of the eye enlargement implant 30 in a radial direction with respect to the center of the eyeball by using a scalpel, to thereby form an incised portion 40 (Step B).

When the incised portion 40 is formed, the practitioner (doctor) holds the grip 56 of the insertion space securement instrument 52 illustrated in FIG. 7 to push and insert the tip portion thereof in one direction, for example, a counter-clockwise direction (see an arrow illustrated in FIG. 4) through the incised portion 40. Thereby, as the insertion space securement instrument 52 is inserted under the conjunctiva thereof, the conjunctiva and the sclera that have been in close contact with each other become separated from each other, and thus an insertion space is secured (Step C).

When the tip portion of the insertion space securement instrument 52 turns around the cornea in the counter-clockwise direction and reaches a side opposite to the incised portion 40, that is, a position of about 180 degrees, the practitioner (doctor) stops the inserting operation for securing a space, retracts the insertion space securement instrument 52 in a direction opposite to an advancing direction, and pulls out the same from the incised portion, then a first space securing operation is completed (Step D).

Next, the tip portion of other insertion space securement instrument 52, which is symmetrical with the insertion space securement instrument 52, or the insertion space securement instrument 52, which is collected by being pulled out of the eyeball and is turned over, is inserted into the eyeball through the incised portion 40. However, the tip portion is inserted, for example, in the counter-clockwise direction in the first space securing operation, whereas at this moment, the tip portion is pushed and inserted into the eyeball in a direction opposite thereto, that is, in a clockwise direction (see a dashed-line arrow illustrated in FIG. 4). Accordingly, the insertion space securement instrument 52 turns around the cornea while enlarging the space between the conjunctiva and the sclera that have been in close contact with each other, and the tip portion thereof reaches a side opposite to the incised portion 40, that is, a position of 180 degrees, and as a result, gap spaces on both sides of the eyeball communicate with each other. In this state, the practitioner (doctor) retracts the insertion space securement instrument 52 again, and pulls out the same through the incised portion 40, then a second space securing operation is completed (Step E).

When a ring-shaped gap having a predetermined width is formed between the conjunctiva and the sclera by enlarging the conjunctiva using the insertion space securement instrument 52, the eye enlargement implant 30 is inserted into the gap. To this end, the hook 64 formed at the tip portion of the semicircular insertion instrument body 60 of the insertion instrument 58 illustrated in FIGS. 10 and 11 is inserted into the hooking hole 50 formed in the tip portion of the eye enlargement implant 30 so as to be locked thereto from bottom to top (or from top to bottom). Then, the hook 64 of the tip portion thereof is pushed into the gap between the conjunctiva and the sclera through the incised portion 40 in the counter-clockwise direction (or the clockwise direction). When the eye enlargement implant 30 is inserted together therewith using the insertion instrument 58 through the incised portion 40, since the gap is formed between the conjunctiva and the sclera in advance, the two instruments 30 and 58 are smoothly inserted along the gap. When the tip portion of the hook is inserted at a position of 180° which is a side opposite to the incised portion 40, further inserting operation is not performed, and the insertion instrument 58 is pulled out by retracting. When the insertion instrument 58 is retracted in an opposite direction along a movement trajectory at the time of insertion, the hook 64 is taken out from the hooking hole 50, and then when the practitioner (doctor) pulls out the insertion instrument 58 in a circular motion, the semicircular insertion instrument body 60 of the insertion instrument 58 is finally pulled out of the incised portion 40. In this state, one half of the body of the eye enlargement implant 30 is inserted into the eyeball, that is, the tip portion in which the hooking hole 50 is formed is located at a position of 180 degrees which is the side opposite to the incised portion 40, the tip portion is within the eyeball, and the other half of the body of the eye enlargement implant 30 remains outside the eyeball (Step F).

In the next step, the tip portion of the semicircular pulling-out instrument body 68 of the pulling-out instrument 66 illustrated in FIGS. 12 and 13 is pushed through the incised portion 40 in an opposite direction, that is, since a part of body of the eye enlargement implant 30 is located on a right side of the eyeball 10 based on FIG. 4, in a left direction of the incised portion 40, and is inserted into the eyeball in a circular motion with respect to the left outer periphery of the eyeball in the clockwise direction. When the tip portion of the pulling-out instrument body 68 reaches the tip portion of the eye enlargement implant 30, the hook 74 is further advanced so as to slightly pass the hooking hole 50, and the pulling-out instrument 66 is retracted and allows the hook 74 to be locked to the edge portion of the hooking hole 50. When the hook 74 is locked to the edge portion of the hooking hole 50, the hook 74 is continuously pulled out, and thereby, the eye enlargement implant 30 locked with the hook 74 also moves together. By doing so, when the hook 74 of the pulling-out instrument 66 is taken out from the incised portion 40, the end portion 46 having the hooking hole 50 of the eye enlargement implant 30 locked with the hook 74 is also pulled out of the eyeball through the incised portion 40 (Step G).

When the eye enlargement implant 30 is seated on the outer periphery of the cornea of the eyeball in a ring shape, the practitioner (doctor) cuts out a surplus overlapping end portion having the hooking hole 50, that is, brings both end portions thereof into contact with each other at the boundary 44 thereof as illustrated in FIG. 5, or cuts the surplus portion, with some portion left so as to allow both end portions to be slightly overlapped (Step H). After the cutting, the both end portions are sutured with each other (Step I), and then, when the incised portion 40 of the conjunctiva is sutured (Step J), all the procedures are ended. As illustrated in FIG. 15, in a case in which the eye enlargement implant 30 is inserted between the conjunctiva 24 and the sclera 26 in a ring shape so as to surround the outer periphery of the cornea 22 of the eyeball, when other people look at the eyes, the diameter of the eye appears to be enlarged by the eye enlargement implant 30 which looks in the color substantially the same as or similar to that of the iris. Accordingly, the eye looks bigger and crisper (the size of the eye before the procedure is the diameter dl, but after the procedure, the eye looks bigger to the diameter D1).

As described above, according to the present invention, when the eye enlargement implant 30 is not required, the conjunctiva 24 is incised again to form the incised portion, and the eye enlargement implant 30 is easily pulled out, and then the conjunctiva 24 is sutured again, to thereby return the eyeball to the original state. In addition, the cosmetic effect of allowing the eye to look bigger can be obtained safely without side effects such as vision loss or eye inflammation.

Although the present invention has been described with reference to the embodiments shown in the drawings, but these are merely an example. It should be understood by persons having common knowledge in the technical field to which the present invention pertains that various modifications and modifications of the embodiments may be made therefrom. Therefore, it should be understood that the present invention is not limited to the specific embodiments shown and described herein. Accordingly, the real technical protection scope of the present invention is determined by the technical spirit of the appended claims. It also should be understood that the present invention includes all modifications, equivalents, and alternatives falling within the spirit and scope of the present invention as defined by the appended claims.

DESCRIPTION OF REFERENCE NUMERALS

10: eyeball, 12: crystalline lens
14: vitreous body, 16: iris
18: retina, 20: macula
22: cornea, 24: conjunctiva
26: sclera, 28: pupil
30: eye enlargement implant, 32: inner edge portion
34: lower curved portion,
36: upper curved portion
38: outer edge portion, 40: incised portion
42: ring-shaped body, 44: cutting part (suturing part)
46, 48: end portion, 50: hooking hole
52: insertion space securement instrument, 54: semicircular ring-shaped instrument
56: grip, 58: insertion instrument
60: semicircular insertion instrument body, 62: grip
64: hook, 65: opening groove
66: pulling-out instrument (insertion instrument), 68: semicircular pulling-out instrument body
70: grip, 72: opening groove
74: hook
d1: inner diameter of eye enlargement implant
D1: outer diameter of eye enlargement implant
b: width
t1: maximum thickness
b1: sectional width

The invention claimed is:

1. An eye enlargement implant for beauty of eyes, comprising:
   a ring-shaped body which
   has an inner diameter portion and an outer diameter portion, wherein the inner diameter portion has a size enough to surround an outer periphery of a cornea, and having a width size of 0.8 to 1.2 mm between the inner diameter portion and the outer diameter portion and having a maximum thickness of 0.05 to 0.20 mm at a center portion in a cross section taken in a width direction thereof,
   the ring-shaped body being made of a material having flexibility, and being provided with a cutting part to provide a first end portion and a second end portion,
   wherein the first end portion and the second end portion overlap, and
   wherein a hooking hole is formed in at least one of the first end portion and the second end portion.

2. The eye enlargement implant for beauty of the eyes according to claim 1, wherein the ring-shaped body is made by including at least one material selected from a silicone derivative, polyamide, polyhydroxyethyl methacrylate (PHEMA), polyvinyl pyrrolidone (PVP), polyvinylidene difluoride, methyl methacrylate-acrylic acid polymer (RPG), cellulose acetate butyrate (CAB) and polymethyl methacrylate (PMMA).

3. A pair of instruments for inserting and removing the eye enlargement implant into an eyeball according to claim 1, comprising:

an insertion instrument made of a metal alloy material, a plastic material or a silicone material for a surgical instrument, and which comprises: a semicircular insertion instrument body which is provided with a U-shaped hook which is opened toward an outer end; and a grip formed at the other end portion of the insertion instrument body facing the hook, and a pull-out instrument made of a metal alloy material, a plastic material or a silicone material for a surgical instrument, and which comprises: a semicircular pull-out instrument body which is provided with a U-shaped hook having a groove which is opened toward an inner; and a grip formed at the other end portion of the pull-out instrument body facing the hook, whereby the insertion instrument is configured to lock the U-shaped hook to the hooking hole of the eye enlargement implant, whereby the insertion instrument is adapted to push the eye enlargement implant in one direction through an incised portion formed in a conjunctiva into a gap formed between the conjunctiva and a sclera that surrounds an outer periphery of the cornea, and when the tip portion of the eye enlargement implant reaches a side opposite to the incised portion, to retract and collect the hook with the eye enlargement implant being left; and whereby the pull-out instrument body is configured to be inserted through the incised portion into the gap to engage the hook with the hooking hole of the eye enlargement implant to be locked and to pull the eye enlargement implant towards the incised portion.

4. A pair of instruments comprising an insertion instrument for inserting the eye enlargement implant according to claim 2 between a conjunctiva and a sclera of an eyeball and a pull-out instrument for pulling out the eye enlargement implant, the instruments for inserting and pulling out the eye enlargement implant into the eyeball are characterized in that:

the insertion instrument is made of a metal alloy material, a plastic material or a silicone material for a surgical instrument, and comprises: an insertion instrument body configured for insertion between the conjunctiva and the sclera through an incised portion formed in the conjunctiva so as to be inserted into the eyeball in one direction thereof in a circular motion along an outer periphery of the eyeball; a U-shaped hook having a groove which is opened toward an outer side so as to be inserted into and locked to a hooking hole formed in one end portion of the eye enlargement implant at a tip portion of the insertion instrument body; and a grip formed at the other end portion of the insertion instrument body facing the hook, and the insertion instrument body is formed in a semicircular body configured to insert the hook thereof into the hooking hole of the eye enlargement implant to be locked, and in this state, to be inserted by pushing it in one direction of the eyeball through the incised portion in a circular motion along the outer periphery of the eyeball, and when a tip portion of the eye enlargement implant reaches a point on a side opposite to the incised portion, to retract the hook in a circular motion again along the same trajectory as when inserting with the eye enlargement implant being left so as to pull out the hook to an outside through the incised portion, and the pull-out instrument is made of a metal alloy material, a plastic material or a silicone material for a surgical instrument, and comprises: an pull-out instrument body configured for insertion between the conjunctiva and the sclera through an incised portion formed in the conjunctiva so as to be inserted into the eyeball in the other direction thereof which is a direction opposite to a direction in which the insertion instrument is inserted in a circular motion along an outer periphery of the eyeball; a U-shaped hook having a groove which is opened toward an inner side so as to be inserted into and locked to the hooking hole of the eye enlargement implant at a tip portion of the pull-out instrument body; and a grip formed at the other end portion of the pull-out instrument body facing the hook, and the pull-out instrument body is formed in a semicircular body configured to start to be inserted through the incised portion toward a direction opposite to a direction in which the eye enlargement implant inserted in the eyeball enters and to be inserted into the eyeball in a circular motion along the outer periphery of the eyeball, then insert the hook thereof into a hooking hole formed in the tip portion of the eye enlargement implant to be locked, and in this state, to be pulled-out in a circular motion again along the same trajectory as when inserting so as to pull out an end portion provided with the hooking hole to an outside of the eye ball through the incised portion.

* * * * *